United States Patent [19]

Hsieh

[11] Patent Number: 5,331,682

[45] Date of Patent: Jul. 19, 1994

[54] RADIATION DETECTOR OFFSET AND AFTERGLOW COMPENSATION TECHNIQUE

[75] Inventor: Jiang Hsieh, Waukesha, Wis.

[73] Assignee: General Electric Company, Milwaukee, Wis.

[21] Appl. No.: 797,641

[22] Filed: Nov. 25, 1991

[51] Int. Cl.⁵ .................................. A61B 6/03
[52] U.S. Cl. ........................ 378/19; 378/901; 364/413.15
[58] Field of Search .................. 378/4, 901; 250/252.1 R; 364/413.4, 413.19, 413.17, 413.14

[56] References Cited

U.S. PATENT DOCUMENTS

| | | | |
|---|---|---|---|
| 4,112,303 | 9/1978 | Brandt | 250/445 T |
| 4,233,662 | 11/1980 | LeMay | 364/414 |
| 4,494,141 | 1/1985 | Altekruse | 358/111 |
| 4,583,240 | 4/1986 | Gatten et al. | 378/19 |
| 5,249,123 | 9/1993 | Hsieh | 364/413.19 |
| 5,265,013 | 11/1993 | King et al. | 364/413.21 |

Primary Examiner—Paul M. Dzierzynski
Assistant Examiner—Daniel V. Bruce
Attorney, Agent, or Firm—Quarles & Brady

[57] ABSTRACT

A computed tomography imaging system includes a source of radiation and a detector that produces an output signal representing sensed radiation from the source. Prior to using the system to produce an image, the source produces a pulse of radiation and the detector output signal is periodically sampled until the output signal has decayed to a negligible level. These samples form values which define a standard response of the detector. Thereafter when image samples are acquired, a decaying output signal from detector is sampled after radiation production terminates. The decay samples are compared to the standard response and coefficients defining the comparison are found. The coefficients and the standard response data are used to derive compensation values which are arithmetically applied to the image samples thereby producing compensated samples. An image is reconstructed from the compensated samples.

10 Claims, 3 Drawing Sheets

RADIATION DETECTOR OFFSET AND AFTERGLOW COMPENSATION TECHNIQUE

BACKGROUND OF THE INVENTION

The present invention relates to radiation detectors such as those used in computed tomography imaging systems; and particularly to techniques which compensate for offset and afterglow errors in output signals from the detectors.

As shown in FIG. 1, a computed tomography (CT) scanner for producing images of the human anatomy includes a motorized patient table 10 which positions a patient at different depths within aperture 11 of a gantry 12. A source of highly collimated X-rays 13 is mounted within the gantry 12 to one side of its aperture 11, and one or more detectors 14 is mounted to the other side of the aperture. The X-ray source 13 and detectors 14 revolve about aperture 11 during a scan of the patient to obtain X-ray attenuation measurements from many different angles.

A complete scan of the patient is comprised of a set of X-ray attenuation measurements which are made at different angular orientations of the X-ray source 13 and detector 14. The gantry may stop or continue to move as the measurements are being made. The measurement at a given orientation is referred to in the art as a "view" and the set of measurements at a view forms a transmission profile. As shown in FIG. 2, the X-ray source 13 produces a fan-shaped beam which passes through the patient and impinges on an array of detectors 14. Each detector 14 in this array produces a separate attenuation signal and the signals from all the detectors 14 are separately acquired to produce the transmission profile for the indicated angular orientation. The X-ray source 13 and detector array 14 continue to revolve in direction 15 to a another angular orientation where the next transmission profile is acquired.

The resultant transmission profiles from the scan then are used to reconstruct an image which reveals the anatomical structures in a slice taken through the patient. The prevailing method for reconstructing image is referred to in the art as the filtered backprojection technique. The attenuation measurements are converted to integers called "CT numbers" or "Hounsfield units", which are used to control the brightness of a corresponding pixel on a CRT display.

Typically a number of scans are taken as the table 10 moves into aperture 11 to produce image slices through the patient at different locations. It is desirable to minimize the period between scans to reduce the overall time of the patient examination. Presently available systems have a one second inter-scan period. However the response of the radiation detector 14 is not instantaneous and such short inter-scan periods result in the detector retaining residual effects from the previous scan when the next scan begins.

Specifically, each X-ray detector 14 in the array comprises a scintillator and a solid state photodiode. X-rays striking the scintillator produce light photons which are absorbed by the photodiode creating an electric current. The light is not emitted by the scintillators instantaneously, rather the emission follows a multi-exponential curve. Similarly the light emission does not terminate immediately at time $T_0$ when the X-ray beam is extinguished, but produces a signal from the detector which decays with a multi-exponential curve function as shown in FIG. 3. The time dependence of the output signal intensity can be modelled accurately as a sum of several different time constants components. The shortest of the decay components has a time constant on the order of one millisecond and is referred to herein as the "primary speed". The primary speed component accounts for most of the residual output from the detector after the X-ray beam is extinguished. However, the remaining components can have time constants as long as several hundred milliseconds.

Because the detector array is rotating rapidly about the patient, the exponential decay blurs together detector readings for successive views creating an adverse effect that is referred to as "afterglow". The afterglow is a function of the intensity of the X-ray flux and the response characteristics of the detector. U.S. Pat. No. 5,249,123 entitled "Compensation of Computed Tomography Data for Detector Afterglow Artifacts", filed concurrently herewith, describes a technique which can be employed to compensate for afterglow effects during each scan. However, when a relatively short amount of time exists between consecutive scans, the afterglow from the previous scan affects the detector signal for the subsequent scan. The afterglow degrades the azimuthal component of the image resolution which produces shading and arc shaped artifacts in the reconstructed image. The azimuthal direction 16 of the image area is perpendicular to a line 17 from the center of the imaging aperture 11. Thus it is desireable to compensate for afterglow effects from one scan to the next.

Another error is an offset $A_0$ of the detector signal in FIG. 3 due to an number of factors, such as the dark current of the detector and thermal drift. Previously, the dark current was measured prior to each scan, when radiation is not striking the detector, and the measurement was used to derive a dark current compensation value. This compensation value is applied to subsequent detector signals to remove the offset due to the dark current. Thermal and time dependent factors also contribute to the overall offset error and vary the offset from scan to scan.

The dynamic offset components for each detector in the array can be measured between scans to generate compensation values. However, the measurement heretofore could not be made until sufficient time had elapsed after the beam extinguished to allow the afterglow to decay to a negligible level. The afterglow decay can last 600 milliseconds or more. In addition, the X-ray source 13 has a non-instantaneous response producing a delay between the shut-off of the source and the extinction of the X-ray beam. Taking into account all of these factors a three second waiting period is required after a scan before offset data acquisition can start. As the operating speed of CT systems increase, even a three second delay prolongs image acquisition and makes the process more susceptible to errors from patient movement. As a consequence it is desirable to be able to acquire data for offset compensation without having to wait for the afterglow to decay to a negligible level.

SUMMARY OF THE INVENTION

A medical imaging system, such as one using computed tomography, includes a source of radiation and an array of detectors which senses radiation from said source. Each detector produces an output signal indicative of the sensed radiation and has an exponentially decaying impulse response that is characterized by a plurality of different time constant decay components.

Prior to using the system to produce an image, for example during system manufacture, the source is excited to produce a pulse of radiation. Samples of the detector output signal are acquired until the output signal generated in response to the radiation pulse has decayed totally. These samples form values which define a standard response of the detector to radiation and are stored in the imaging system as a bench mark. The effects of detector dark current preferably are removed from the standard response values before storage. In practice, it is preferred to acquire and average multiple sets of these signal samples in order to reduce statistical noise from the standard response data.

During subsequent operation of the system to produce an image, a decaying output signal from the detector is sampled after the radiation terminates. The decay samples and the standard response data are compared to detect a change in the response of the detector. A set of coefficients are produced which define the comparison. The coefficients are arithmetically applied to standard response data to generate a series of compensation values. Each compensation value corresponds temporally with reference to the extinction of the radiation to an attenuation measurement value acquired during an image scan. The corresponding compensation value is applied to the attenuation measurement value to produce a compensated value. For example, the compensation value is subtracted from the image signal sample. An image is reconstructed from the compensated values.

A general object of the present invention is to provide a compensation mechanism for the time varying effects imposed on the detector output signal by offsets and afterglow.

Another object is to provide a technique which measures the offset effect between scans of CT imaging system without waiting until the afterglow has died.

DESCRIPTION OF THE PRESENT INVENTION

Figure 1:
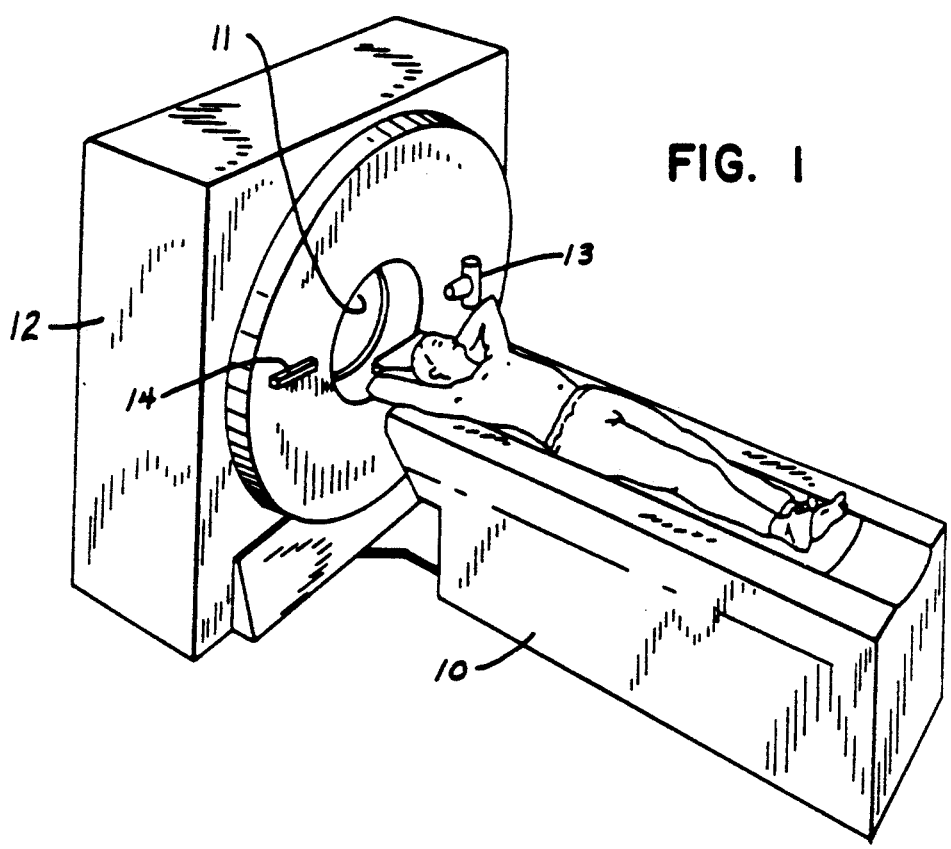
FIG. 1 is a perspective view of a CT imaging system in which the present invention may be employed.
Figure 2:
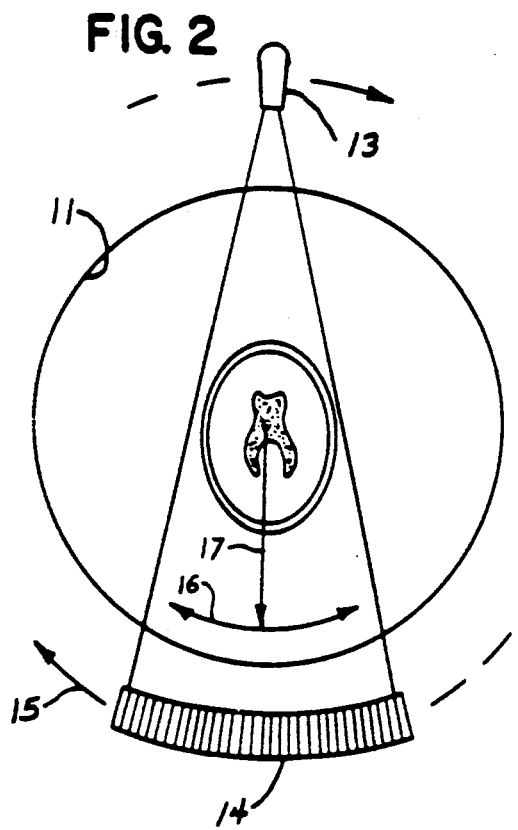
FIG. 2 is a schematic representation of a scanning technique employed in the CT imaging system.
Figure 3:
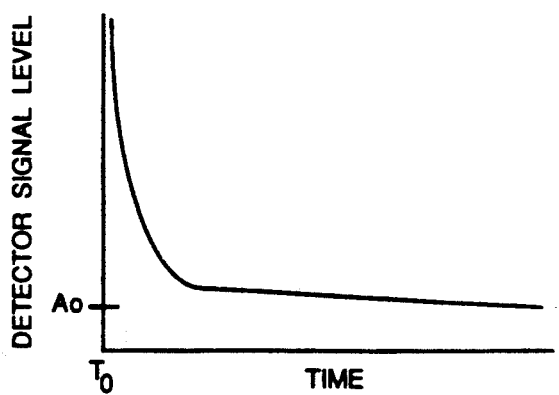
FIG. 3 is a graph illustrating the afterglow and offset of a signal produced by the radiation detector in the CT imaging system.
Figure 4:
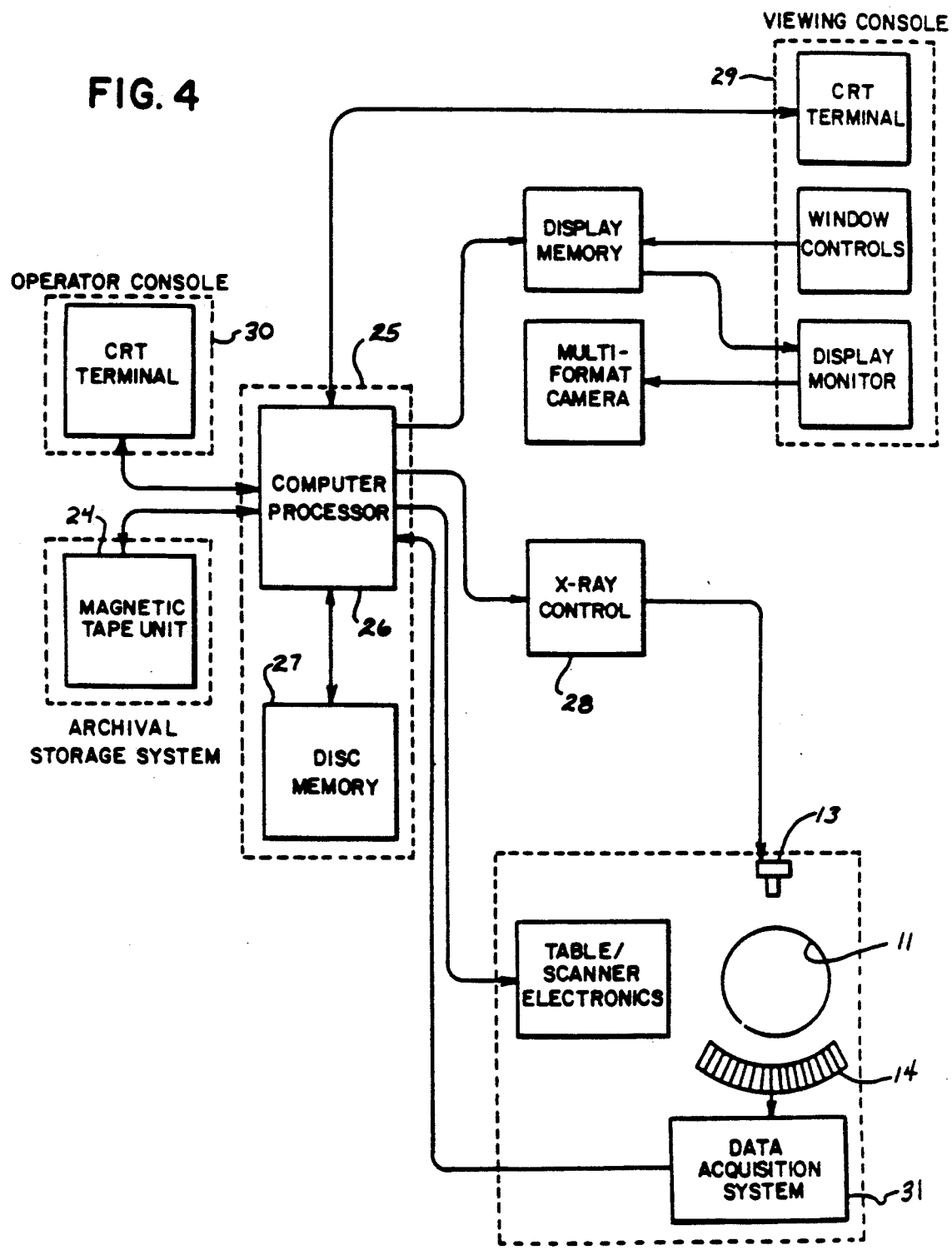
FIG. 4 is a block diagram of processing circuitry for processing signal from the radiation detector.

With reference to FIGS. 1, 2 and 4, the operation of the CT imaging system is controlled by a programmable data processing system 25 which includes a computer processor 26 and a disc memory 27. The disc memory 27 stores the programs that the computer processor 26 uses in patient scanning and in image reconstruction and display. It also stores, on a short-term basis, the acquired data and the reconstructed image data. The computer processor 26 includes a general purpose minicomputer and an array processor with input and output ports suitable for connection to the other system components as shown.

An output port on the computer processor 26 connects to an X-ray control circuit 28, which in turn controls excitation of the X-ray source 13. The high voltage on the X-ray source 13 is controlled and its cathode current is regulated to provide the correct dosage. The high voltage and cathode current are selected by a user who enters the desired values through an operator console 30 and the computer processor 26 directs the production of the X-rays in accordance with its scan program.

The X-rays disperse in a fan-shape described previously and are received by the array of detectors 14 mounted on the opposite side of the gantry aperture 11. Each detector examines a single ray originating from the X-ray source 13 and traversing a straight line path through a patient located in the aperture 11. The detector array also includes a group of reference detectors at each of its ends that receive unattenuated X-rays from the source 13. The currents formed in each detector 14 are collected as an analog electrical signal and then converted into a digital number by analog to digital converters in a data acquisition system 31. The signals are digitized sequentially starting at one end of the detector array and finishing at the other end. The digitized signal samples from all the detectors form a complete view and are fed to the computer processor 26.

U.S. Pat. Nos. 4,112,303 and 4,115,695 disclose the details of the gantry construction, U.S. Pat. No. 4,707,607 describes the detector array 14, and the data acquisition system is disclosed in U.S. Pat. No. 4,583,240. An array processor suitable for use in the computer processor is disclosed in U.S. Pat. No. 4,494,141. The descriptions of these components in the cited patents are incorporated herein by reference.

The digitized attenuation measurements from the data acquisition system 31 are preprocessed to compensate for uneven detector sensitivities and gains, as well as variation of the X-ray beam intensity throughout the scan. This is followed by beam hardening corrections and conversion of the data to logarithmic form so that each measured value represents a line integral of the X-ray beam attenuation. The preprocessing is performed in real-time while the scan is occurring. The raw attenuation values in each view are stored as one row of a two-dimensional raw data array in the disc memory 27. Each of these rows of attenuation data provides a transmission profile of the object to be imaged when viewed from a single angle. Each column of data in the array represents the data acquired from a given detector during the scan. For example, signals from up to 852 detectors may be sampled approximately 1000 times during a scan to produce an equivalent number of views.

Figure 5:
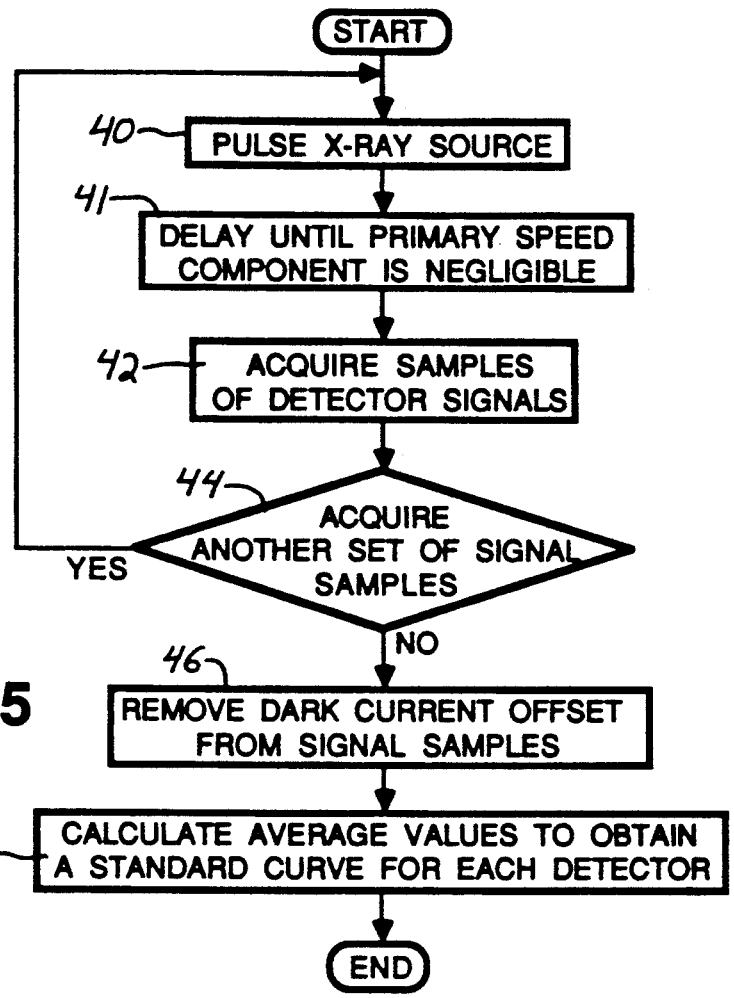
FIG. 5 is a flowchart of a process for obtaining a set of data which characterizes the standard response of the radiation detector.

The present CT system utilizes a unique process which compensates for the offset and afterglow effects in the raw attenuation values in the data array. During manufacture of the CT system, data representing a "standard response curve" $X_i(t)$ is acquired as a bench mark for a each detector (i) in the array 14. The standard response curve is produced by the computer processor according to the steps depicted in the flowchart of FIG. 5.

Commencing at step 40, the X-ray source 13 is excited for a fixed period of time which is sufficiently long so that the signal from the detector 14 will reach its full magnitude in response to the X-radiation. The source then is turned off and the process delays at step 41 for a time which is sufficient for the X-ray beam to be extinguished and for the primary speed component of the detector's exponential decay to reach a negligible level. The delay interval may be eighty milliseconds in duration, although the length of the delay is dependent upon the type of detector. Since the primary speed component dies very quickly, it does not affect the subsequent scan and need not be considered in the compensation.

After waiting for the prescribed period, the output of each of the detectors in array 14 is periodically sampled at step 42. The sampling occurs approximately every millisecond for a sufficiently long period to acquire samples of the longest time constant component of the detector response decay. For example, a sampling period of two seconds has been found to be adequate for one type of radiation detector in this manner. In order to improve the accuracy of the derivation of the standard response curve, several sets of afterglow data are acquired from each detector. Therefore, at step 44 a determination is made whether additional sets of data are desired and if so the process returns to step 40.

Once a sufficient number of sets of detector signal samples have been acquired, the process advances to step 46 where the dark current offset is removed from the samples in all of the sets. A value for the dark current offset was derived previously using a conventional technique. Then at step 48, the sets of data for a given detector are averaged to produce a set of reference data for the standard response curve of that detector. These standard response curves serve as bench marks for characterizing the afterglow of each detector. The averaged sets of data samples are stored as an array within the disk memory 27 of the CT system.

Figure 6:
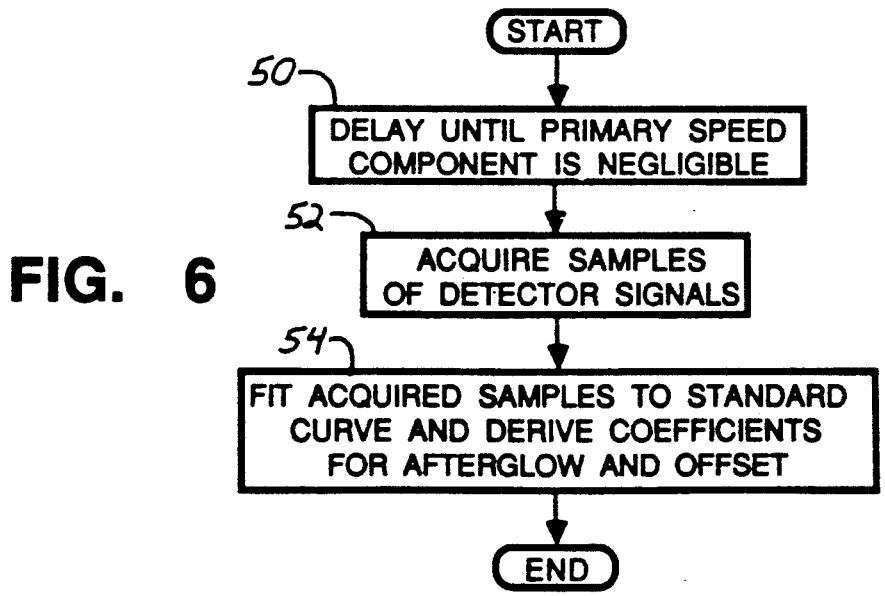
FIG. 6 is a flowchart of a portion of the present invention which calculates offset and afterglow compensation values.

The standard response curves stored in the CT system are used at the beginning of each image acquisition scan to compensate for any afterglow effects from the previous scan and for dynamic offset variation. The first phase of this compensation is the acquisition of data at the end of the last view of a scan. When the X-ray source 13 is shut off to terminate the last view of the scan, the computer processor 26 begins executing the process disclosed in FIG. 6 which produces a set of compensation coefficients. In order to produce these coefficients, the process delays at step 50 for a period of time sufficient for the effects of the primary speed component of the detector response decay to reach a negligible level. This interval should be the same as that used at step 41 to produce the standard response curve (e.g. 80 milliseconds).

Then at step 52, the signals from the detectors in array 14 are sampled at the same interval that they were sampled at step 42 to produce the standard response curve (e.g. one millisecond). Each of these newly acquired samples is stored in a separate array for each detector. As the inter-scan interval is significantly shorter than the period of time required for the afterglow to decay totally, the detector signals can only be sampled for a portion of the afterglow. For real-time processing, time must remain in the inter-scan period after the acquisition of signal samples to calculate the compensation coefficients before the beginning of the next scan. For example, if the inter-scan period is one second and an eighty millisecond delay occurs before the acquisition of the samples, a 500 millisecond sampling period is utilized so that sufficient time remains before the next scan during which to calculate the compensation coefficients for all the detectors. It is apparent that the sampling period depends upon not only the duration of the inter-scan interval, but also the computing speed of the processor 26. If real-time processing is not required, the afterglow sampling period may extend to just before the next scan starts. In this case, the raw data from the next scan is stored temporally and the compensation process is performed at the completion of data acquisition. The present compensation concept will be described in the context of real-time processing.

Once all of the samples $Y_i(t)$ have been acquired, the data set is least square fitted to the standard response curve data $X_i(t)$ for the following first order polynomial:

$$Y_i(t) = \alpha X_i(t) + \Psi \quad (1)$$

The curve fitting process yields values for $\alpha$, which represents the strength of the afterglow, and $\Psi$ which represents the size of the dynamic offset. The calculation of the coefficients $\alpha$ and $\Psi$ by curve fitting the data acquired between scans for each detector with that detector's standard response curve is accomplished before the next scan begins.

As noted previously, the next scan begins approximately one second after the termination of the previous scan. When the first data sample for the next scan is acquired, the computer section 26 reads the data sample of the standard response curve which was acquired one second after the termination of the X-ray pulse that was used to produce the standard response curve. This data sample corresponds temporally with the first data sample of the next scan with respect to the effects of afterglow from the previous scan. A similar temporal correspondence exist between other samples of the standard response data and the detector signal.

The corresponding sample of the standard response curve along with the coefficients $\alpha$ and $\Psi$ are applied to equation (1) to produce a compensation value $Z_i(t)$ representing the effects on the new sample due to afterglow and dynamic offset errors. This compensation value is subtracted from the newly acquired data sample to provide a compensated data sample which is stored in an array in disk memory 27. As each detector signal sample of the next scan is acquired, a temporally corresponding data value is obtained from the standard response curve and used along with the compensation coefficients to calculate a correction value for the afterglow and dynamic offset. The calculation of the compensation values and the application of them to the data samples are performed by the array processor in computer processor 26.

Although the output signals from the detector are sampled between scans for a period that was significantly shorter than the exponential decay period, the derivation of the compensation coefficients permits a correction value to be calculated from the standard response curve data for any time during the decay. In addition, the inter-scan period can be substantially shorter than the decay period without affecting the abililty to derive the correction values.

Eventually, the signal samples for the new scan will be acquired sufficiently long after the previous scan terminated that the afterglow will have decayed totally. For example, signal samples acquired several seconds after the previous scan terminated typically will not be affected by the afterglow from that scan. When this occurs, there no longer will be a temporally corresponding data value in the standard response curve and the first term of equation (1) will become zero so that the compensation factor $Z_i(t)$ will consist of only the offset coefficient $\Psi$. Similarly, if a break in the examination process occurs such that the interval between successive scans is greater than two seconds, the first data sample of the next scan will be compensated only for the dynamic offset as the afterglow has decayed totally.

Robustness of the compensation mechanism can be improved by adding a coefficient $\beta t$ to equation (1) which accounts for linear drifts of the offset caused by thermal effects. In situations where such thermal drift is significant, the compensation formula becomes:

$$Y_i(t) = \sum_i a_i X_i(t) + \psi + \beta t \quad (2)$$

The present compensation enables the use of an inter-scan interval that is shorter than the afterglow decay period. The technique characterizes the scan to scan afterglow and dynamic offset utilizing samples of only a portion of the afterglow decay following each scan. The characterizing equations allow the derivation of coefficients for the afterglow and dynamic offset, compensation values can be estimated for any time during the decay. Therefore, such compensation values can be determined for data samples acquired in the succeeding scan based on afterglow and offset sampling carried out in the inter-scan interval.

I claim:

1. A medical imaging system comprising:
    a source of radiation:
    a detector for sensing radiation from said source and producing an output signal representing the sensed radiation, said detector having a radiation response which decay with time, the output signal being affected by an offset which varies temporally;
    a first means for storing a set of values $X_i(t)$ defining a standard response for the detector;
    means for acquiring samples of the output signal periodically from said detector;
    means for receiving a plurality of samples of the output signal that said means for acquiring produced after extinction of radiation;
    means for fitting the plurality of samples to the set of values defining the standard response and deriving coefficients defining a degree of fit;
    means for determining, for a given sample, a compensation value derived from the values defining the standard response of the detector to radiation and from the coefficients defining a degree of it;
    means for arithmetically combining the compensation value and the given sample to produce a compensated sample; and
    means for reconstructing an image from compensated samples.

2. The medical imaging system as recited in claim 1 wherein said means for processing arithmetically derives the compensation value from the coefficients and a value defining the standard response.

3. The medical imaging system as recited in claim 1 wherein said means for processing determines the compensation value $Z_i(t)$ according to the following equation:

$$Z_i(t) = aX_i(t) + y$$

where coefficient a represents the strength of afterglow of the detector, and coefficient y represents an output signal offset.

4. The medical imaging system as recited in claim 1 wherein said means for processing arithmetically derives the compensation value $Z_i(t)$ according to the following equation:

$$Z_i(t) = \sum_i a_i X_i(t) + y + bt$$

where coefficient a represents the strength of afterglow of the detector, coefficient y represents an output signal offset, and coefficient bt represents a thermal drift effect on the output signal.

5. A method for processing data in a medical imaging system having a source of radiation and a detector that produces an output signal representing the sensed radiation, steps of said method comprising:
    acquiring a set of values which define a standard response of the detector to radiation, said acquiring including activating the source to produce a pulse of radiation and producing a set of samples of the output signal from the detector until the output signal has decayed to substantially zero magnitude;
    acquiring samples of the output signal periodically from said detector;
    determining, for a sample of the output signal, a compensation value derived from the values representing the standard response of the detector to radiation;
    arithmetically combining the compensation value and the given sample to produce a compensated sample; and
    reconstructing an image from compensated samples.

6. The method as recited in claim 5 wherein the step of acquiring a set of values which define a standard response of the detector further comprises removing the effect of dark current from the set of samples of the output signal.

7. A method for processing data in a medical imaging system having a source of radiation and a detector that produces an output signal representing the sensed radiation, steps of said method comprising:
    acquiring a set of values which define a standard response of the detector to radiation;
    acquiring samples of the output signal periodically from said detector;
    receiving a plurality of samples of the output signal from said detector after extinction of radiation, which plurality of samples represents at least a portion of afterglow of the detector;
    fitting the plurality of samples to the set of values defining a standard response and deriving coefficients defining a degree of fit;
    determining, for a sample of the output signal, a compensation value derived from a coefficient defining a degree of fit;
    arithmetically combining the compensation value and the given sample to produce a compensated sample; and
    reconstructing an image from compensated samples.

8. The method as recited in claim 7 wherein said step of determining a compensation value arithmetically derives the compensation value from the coefficients and a value defining the standard response of the detector.

9. The method as recited in claim 7 wherein said step of determining a compensation value $Z_j(t)$ does so according to the following equation:

$$Z_j(t) = aX_j(t) + y$$

where coefficient a represents the strength of afterglow from detector, and coefficient y represents an output signal offset.

10. The method as recited in claim 7 wherein said step of determining a compensation value $Z_j(t)$ does so according to the following equation:

$$Z_j(t) = \sum_i a_i X_i(t) + y + bt$$

where coefficient a represents the strength of afterglow from the detector, coefficient y represents an output signal offset, and coefficient bt represents a thermal drift effect on the output signal.

* * * * *